(12) United States Patent
Seo et al.

(10) Patent No.: US 7,888,286 B2
(45) Date of Patent: Feb. 15, 2011

(54) METHOD OF SELECTIVELY CONTROLLING MORNING GLORY (IPOMOEA) SPP

(75) Inventors: Seok Weon Seo, Kashiwa (JP); Akira Taniguchi, Nagoya (JP)

(73) Assignee: Bayer CropScience AG (DE)

( * ) Notice: Subject to any disclaimer, the term of this patent is extended or adjusted under 35 U.S.C. 154(b) by 56 days.

(21) Appl. No.: 11/537,858

(22) Filed: Oct. 2, 2006

(65) Prior Publication Data

US 2008/0026945 A1 Jan. 31, 2008

(30) Foreign Application Priority Data

Jul. 28, 2006 (JP) .............................. 2006-205683

(51) Int. Cl.
- *A01N 57/10* (2006.01)
- *A01N 57/18* (2006.01)
- *A01N 57/26* (2006.01)
- *A01N 57/02* (2006.01)

(52) U.S. Cl. ...................................... 504/206
(58) Field of Classification Search ................ 506/206
See application file for complete search history.

(56) References Cited

U.S. PATENT DOCUMENTS

| 3,682,617 A | 8/1972 | Doyle, Jr. |
| 6,534,444 B1 * | 3/2003 | Sievernich et al. ........... 504/128 |
| 2004/0092402 A1 * | 5/2004 | Kuragano et al. ........... 504/242 |

FOREIGN PATENT DOCUMENTS

| EP | 204146 A2 * | 12/1986 |
| EP | 0 299 382 | 1/1989 |
| WO | WO 99/65314 A | 12/1995 |

OTHER PUBLICATIONS

United States Environmental Protection Agency, Report of the Food Quality Protection Act Tolerance Teassessment Progress and Risk Management Decision of Diquat Dibromide, Form 7508C, Apr. 25, 2002.*
Culpepper et al., Weed Technology, 2000, Allen Press, vol. 13, issue 1, pp. 77-88.*
ECOMALL-A Place to Help Save the Earth. Weed Management for the Lawn and Garden[online, updated on May 25, 2005]. Retrieved from the internet:< URL: http://web.archive.org/web/20050525022410/http://www.ecomall.com/greenshopping/washtox.htm, pp. 1-9.*
Lanie et al, "Herbicide combinations for soybean (Glycine max) planted in stale seedbed," Weed Technology, vol. 8, No. 1, 1994, pp. 17-22.

* cited by examiner

*Primary Examiner*—Fereydoun G Sajjadi
*Assistant Examiner*—Courtney Brown
(74) *Attorney, Agent, or Firm*—Frommer Lawrence & Haug LLP

(57) ABSTRACT

A method of selectively controlling morning glory spp., by treating a lower portion of a hill of morning glory spp. with one compound or a combination of two or more compounds selected from glufosinate, L-glufosinate, bialaphos, paraquat, diquat and agriculturally acceptable salts of the compounds.

13 Claims, 4 Drawing Sheets

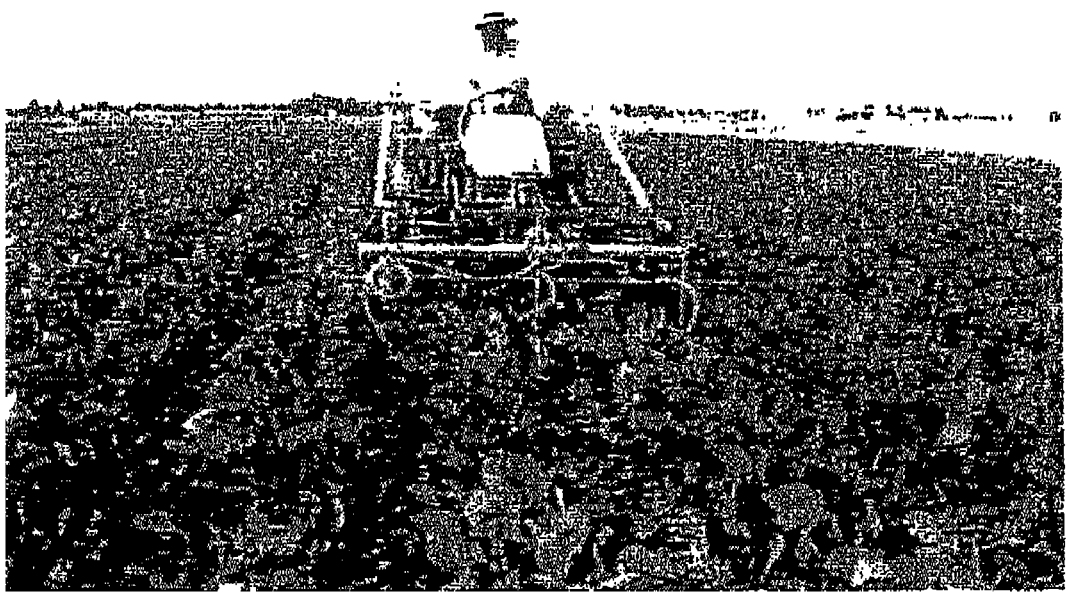
Fig. 1
Fig. 2

Fig. 4
Fig. 5
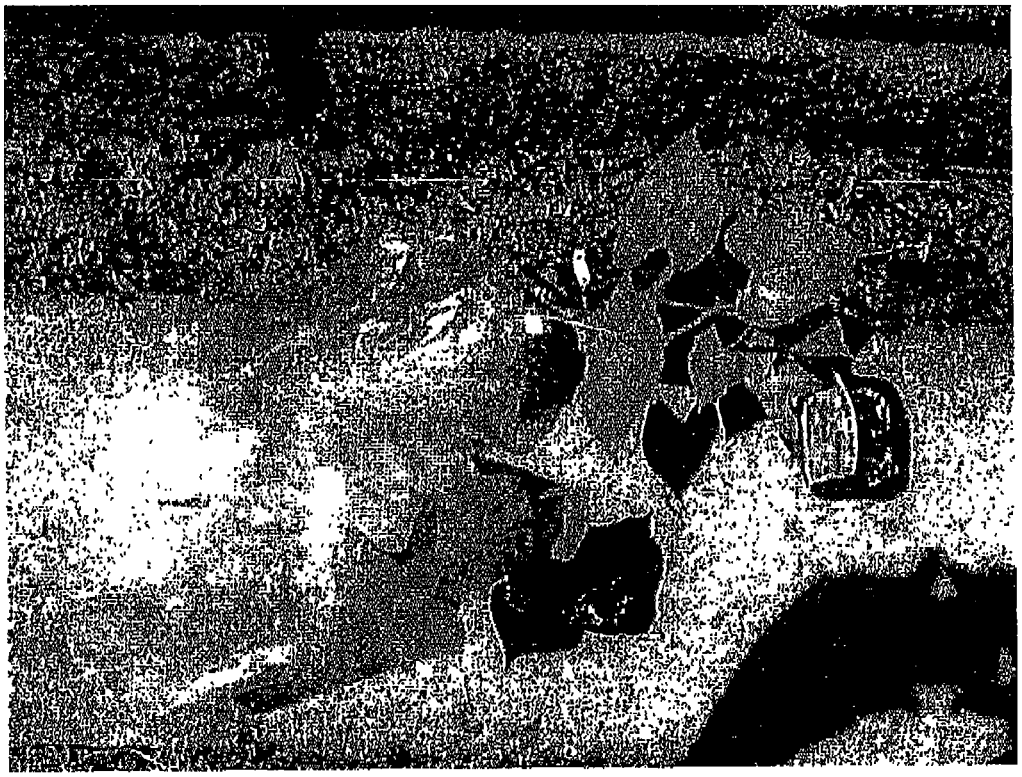

METHOD OF SELECTIVELY CONTROLLING MORNING GLORY (IPOMOEA) SPP

This application claims benefit under 35 U.S.C. 119(a) of Japanese patent application 2006-205683, filed on 28 Jul. 2006.

Any foregoing applications, including Japanese patent application 2006-205683, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SUMMARY OF THE INVENTION

The present invention relates to a method of selectively controlling morning glory (Ipomoea) spp. More specifically, the present invention relates to a method of selectively controlling morning glory spp. by treating a lower portion of morning glory with a certain kind of an active ingredient.

BACKGROUND

Recently, a number of weeds normally not observed in various regions of Japan were found, and control thereof is a problem to be solved. Generation of these weeds is thought to be a result of mixing of seeds of the weeds into imported cereals and disseminating them to the fields as a compost of feces of domestic animals that ate the cereals. The potential for transmission of morning glory spp. seeds makes this a potential problem throughout the world where desired plants are at risk of being destroyed by morning glory spp. Morning glory spp. as one of these weed species are strongly harmful weeds which are vine-like and coil around crops and trees, and which, in some cases, reach several meters in length.

Morning glory spp. can be often observed in soybean fields, paddy field ridge, orchards, dry fields, farm roads, roadsides and the like in Ishikawa, Aichi, Mie, Gifu and Shizuoka prefectures, Tokyo, Chiba prefecture and the like.

For example, in the Tokai region, in soybean fields and some orchards showing generation of morning glory spp. as the most serious problem, there are recognized generations of *Ipomoea hederacea* Jacq., *Ipomoea hederecea* Jacq. var. *integriuscula* A. Gray, *Ipomoea triloba* L., *Ipomoea lacunosa* L., *Ipomoea coccinea* L., *Ipomoea purpurea* Roth and *Ipomoea nil* Roth. Soybean cultivation in the Tokai region is often carried out with large scale by farming associates and large scale farmhouses, and when morning glory spp. prevail in soybean fields and coil around soybean, their control is extremely difficult, and there is no other choice than discard of harvest in some cases. In the case of orchards, when morning glory spp. coil around trees and extend to sites over human reach, their control is extremely difficult.

Various problems due to the generation of morning glory spp. include (i) the germination term of morning glory spp. lasts over a long period, and hence even if they are once controlled, new morning glory generate, (ii) the activities of soil-treating herbicides and selective foliar application herbicides for leaves on morning glory spp. are low, (iii) herbicidal activities of non-selective foliar application herbicides on morning glory spp. differ among herbicides, (iv) difficulty spreading non-selective foliar application herbicides to inter-ridge areas (areas/furrows between ridges of soybean patches) during soybean growth period, and the like.

Citation or identification of any document in this application is not an admission that such document is available as prior art to the present invention.

DESCRIPTION OF THE INVENTION

The present inventors have investigated the above-mentioned problems to found that a herbicidal method set forth below selectively controls morning glory spp.

Thus, the present invention provides a method of selectively controlling morning glory spp., by treating a lower portion of a hill of morning glory spp. with one compound or a combination of two or more compounds selected from the group consisting of glufosinate, L-glufosinate, bialaphos (common name also: bilanafos), paraquat, diquat and agriculturally acceptable salts of the compounds.

The term "hill" of morning glory is a term used in agronomics and generally means the "plant body" (stem and leaves) of morning glory.

The term "selective" or "selectively" for the purposes of this invention means that the kill rate of morning glory spp. is greater than that of the plant desired to be grown. Preferably, the kill rate of morning glory is such that there is little to no adverse effect on the desired plant.

The term "selective" or "selectively" for the purposes of this invention also means that morning glory spp. is affected where it grows and where other plants or areas remain unaffected due to lack of direct treatment with the herbicidal compound.

Surprisingly, according to the present invention, for example, glufosinate (salt) known as a foliar application herbicide is believed to usually kill only the treated portion of a weed due to its property, and show no migrating property of the active ingredient. However, when a lower portion of a hill of morning glory spp. is treated with glufosinate, an acropetal (upper) migrating property is specifically manifested, being capable of killing even stem edge portions not treated of morning glory spp.

Such a distinctive advantageous effect is a surprising one not observed until now, and, due to such controlling method as treating a lower portion of a hill of morning glory spp., the controlling method of the present invention is extremely efficacious and useful for suppressing phytotoxicity on crops in selective control between crops and weeds.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description of the Invention.

BRIEF DESCRIPTION OF DRAWINGS

The following detailed description, given by way of example, but not intended to limit the invention solely to the specific embodiments described, may best be understood in conjunction with the accompanying drawings, in which:

FIG. 1 is a photograph showing full view of spraying of glufosinate (salt).

FIG. 2 is a photograph showing a glufosinate (salt) sprayed part.

FIG. 4 is a photograph showing a killing effect of glufosinate (salt).

FIG. 5 is a photograph showing a killing effect (immediately after spraying) of diquat-paraquat (salts) mixed solution.

DETAILED DESCRIPTION OF THE INVENTION

Figure 3:
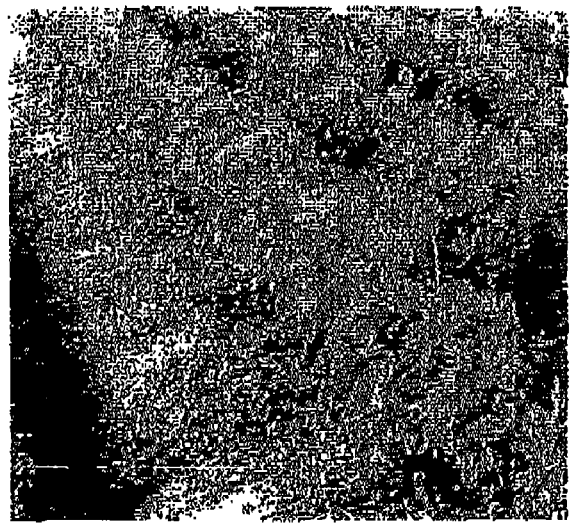
FIG. 3 is a photograph showing a weedkilling process of glufosinate (salt).
Figure 3:
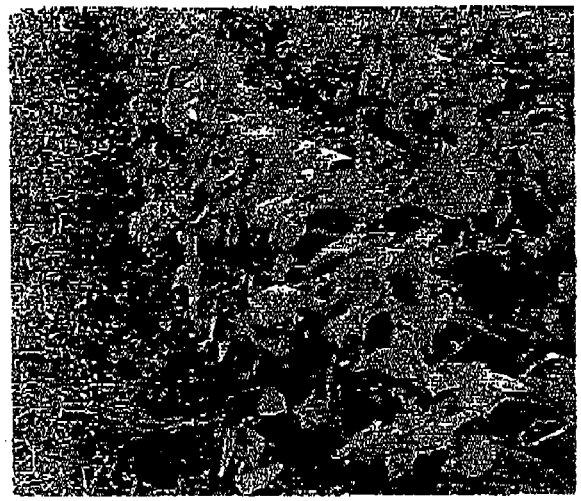
Figure 3:
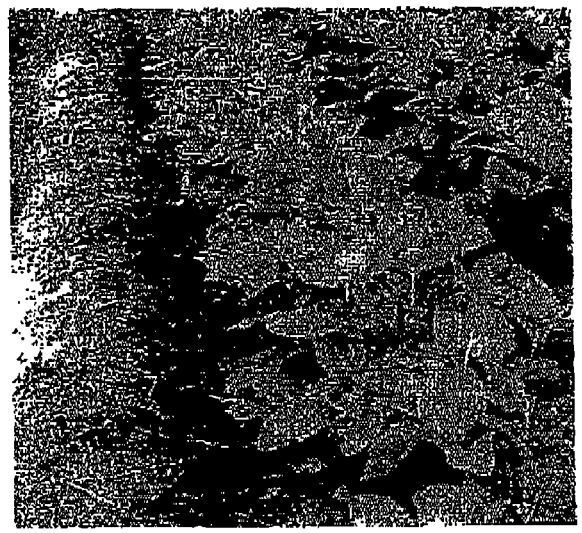

Examples of the compound as the effective ingredient used in the present invention include one or more compounds selected from glufosinate, L-glufosinate, bialaphos (or bilanafos), paraquat and diquat, and agriculturally acceptable salts thereof.

Examples of the combination of two compounds include paraquat and diquat, preferably in form of their commercial salts paraquat dichloride and diquat dibromide.

Preferred examples of the compound include glufosinate (racemic), L-glufosinate, bilanafos and salts thereof, preferably glufosinate ammonium, glufosinate sodium, L-glufosinate ammonium, L-glufosinate sodium and bilanafos-sodium.

The above-mentioned compounds defined by their common names are all known compounds (see, The Pesticide Manual, vol. 13, 2003, published by British Crop Protection Council). L-glufosinate is the herbicidally active optical isomer of the racemic mixture glufosinate.

In the present invention, examples of morning glory spp. as subjects to be controlled include but are not limited to:

*Ipomoea alba* L. (tropical white morning-glory),

*Ipomoea amnicola* Morong (redcenter morning-glory),

*Ipomoea aquatica* Forssk. (swamp morning-glory),

*Ipomoea asarifolia* (Desr.) Roemer & J. A. Schultes (gingerleaf morning-glory),

*Ipomoea barbatisepala* Gray (canyon morning-glory),

*Ipomoea batatas* (L.) Lam. (sweetpotato),

*Ipomoea cairica* (L.) Sweet (mile a minute vine),

*Ipomoea calantha* Griseb. (moonvine),

*Ipomoea capillacea* (Kunth) G. Don (purple morning-glory),

*Ipomoea cardiophylla* Gray (heartleaf morning-glory),

*Ipomoea carnea* Jacq. (gloria de la manana),

*Ipomoea hederecea* Jacq. var. *integriuscula* A. Gray,

*Ipomoea carnea* Jacq. ssp. *fistulosa* (Mart. ex Choisy) D. Austin (gloria de la manana),

*Ipomoea coccinea* L. (redstar),

*Ipomoea coptica* (L.) Roth ex Roemer & J. A. Schultes (alamovine),

*Ipomoea cordatotriloba* Dennst. (tievine),

*Ipomoea cordatotriloba* Dennst var. *cordatotriloba* (tievine),

*Ipomoea cordatotriloba* Dennst var. *torreyana* (Gray) D. AustinTorrey's (tievine),

*Ipomoea cordifolia* Carey ex Voight (heartleaf morningglory),

*Ipomoea costellata* Torr. (crestrib morning-glory),

*Ipomoea cristulata* Hallier f. (Transpecos morning-glory),

*Ipomoea dumetorum* Wilid. ex Roemer & J. A. Schultes (railwaycreeper),

*Ipomoea eggersiana* Peter (jumbypotato),

*Ipomoea eggersii* (House) D. Austin (Egger's morningglory),

*Ipomoea eriocarpa* R. Br. (morning-glory),

*Ipomoea hederacea* Jacq. (ivyleaf morning-glory),

*Ipomoea hederifolia* L (scarletcreeper),

*Ipomoea horsfalliae* Hook. (Lady Doorly's morning-glory),

*Ipomoea imperati* (Vahl) Griseb. (beach morning-glory),

*Ipomoea indica* (Burm. f.) Merr. (oceanblue morning-glory),

*Ipomoea jaegeri* Pilg. (morning glory),

*Ipomoea krugii* Urban (Krug's white morning-glory),

*Ipomoea lacunosa* L. (whitestar),

*Ipomoea leptophylla* Torr. (bush morning-glory),

*Ipomoea žleucantha* Jacq. (pro sp.),

*Ipomoea lindheimeri* Gray (Lindheimer's morning-glory),

*Ipomoea littoralis* Blume (whiteflower beach morningglory),

*Ipomoea longifolia* Benth. (pinkthroat morning-glory),

*Ipomoea macrorhiza* Michx. (largeroot morning-glory),

*Ipomoea mauritiana* Jacq.,

*Ipomoea meyeri* (Spreng.) G. Don (Meyer's morning-glory),

*Ipomoea microdactyla* Griseb. (calcareous morning-glory),

*Ipomoea zmultifida* (Raf.) Shinners (cardinal climber),

*Ipomoea nil* (L.) Roth (whiteedge morning-glory),

*Ipomoea obscura* (L.) Ker-Gawl. (obscure morning-glory),

*Ipomoea ochracea* (Lindi.) G. Don (fence morning-glory),

*Ipomoea pandurata* (L.) G. F. W Mey. (man of the earth),

*Ipomoea pauciflora* Martens & Galeotti (tree morning glory),

*Ipomoea pes-caprae* (L.) R. Br. (bayhops),

*Ipomoea pes-caprae* (L.) R. Br. ssp. *brasiliensis* (L.) van Ooststr. (Brazilian bayhops),

*Ipomoea pes-caprae* (L.) R. Br. ssp. *pes-caprae* (L.) R. Br. [excluded] (bayhops),

*Ipomoea pes-tigridis* L. (morning-glory),

*Ipomoea plummerae* Gray (Huachuca Mountain morning-glory),

*Ipomoea pubescens* Lam. (silky morning-glory),

*Ipomoea purga* (Wender.) Hayne (jalap),

*Ipomoea purpurea* (L.) Roth (tall morning-glory),

*Ipomoea quamoclit* L. (cypressvine),

*Ipomoea repanda* Jacq. (bejuco colorado),

*Ipomoea rupicola* House (cliff morning-glory),

*Ipomoea sagittata* Poir. (saltmarsh morning-glory),

*Ipomoea setifera* Poir. (bejuco de puerco),

*Ipomoea setosa* Ker-Gawl. (Brazilian morning-glory).

In another embodiment of the invention, examples of morning glory spp. as subjects to be controlled include:

*Ipomoea hederacea* Jacq.,

*Ipomoea hederecea* Jacq. var. *integriuscula* A. Gray,

*Ipomoea lacunosa* L.,

*Ipomoea triloba* L.,

*Ipomoea coccinea* L.,

*Ipomoea purpurea* Roth and

*Ipomoea nil* Roth.

The method of the present invention can be adequately used not only for controlling morning glory spp. in the situations of cultivation of useful crops, such as soybean cultivation, fruit cultivation and cotton cultivation, but also for controlling morning glory spp. growing widely in non-agricultural fields and the like.

The advantageous effect of the present invention is observed in situations when the treatment with the herbicidal active ingredient is applied only to a portion of the hill (plant body) of morning glory rather than treatment of the entire plant body. These situations are typical situations where morning glory shall be controlled selectively.

Examples for selective control are for instance control of the weed in the presence of a crop which plant shape allows for a treatment of lower portions of morning glory without substantial treatment of the crop, especially avoiding treatment of the crop leaves. Such crops are, for example, soybean, cotton, grapevine, but also plantation crops of different kind, such as fruit trees (for example apple, pear, quince, peach, plum, olive, pistachios, kiwi fruit citrus crops). In such a case the crop need not or shall not be treated with the herbicidal compounds. The method thus ensures crop safety.

Other examples for selective control is treatment in non-agricultural fields, industrial fields and home- and garden-applications where the method according to the invention allows full control while other useful plants need not be affected.

Similar applications are possible where it is desirous to limit the application to the plants of morning glory in order to avoid treatment of certain areas such as lawn, patches, pathways or part of housings.

The method according to the invention often provides for a reduction in application rate due to avoidance of waste application of areas which need not be treated.

Although only a portion of the plant body has been treated the herbicidal effect surprisingly is observed in all portions of the plant body.

According to the invention the treatment with the herbicidal active ingredient or active ingredient mixture comprises treatment of a lower portion of the plant body of morning glory, preferably comprising treatment of the portion of the plant body emerging from soil up to and including leaf no. 1 (i.e. comprising stem and/or leaf), more preferably up to (and including) subsequent upper leaves of morning glory, such as leaves nos. 1 and 2 or 1, 2 and 3 or 1, 2, 3 and 4 or up to upper leaves, when available while keeping the leave with highest number or a group of leaves with higher numbered leaves untreated.

Leaf (leaves) numbers refer to position of the leaf attached to the plant stem relative to the rootstock (i.e. the underground portion of the morning glory); leaf no. 1 refers to the leaf closest to the rootstock when measured against the length of the plant body; leaf no. 2 refers to the next closest leaf to the rootstock, etc.

For practical purposes the features described have to be interpreted on average and also allows for treatments of a population of plants of morning glory where some of the plants are in different growing states and some of the plants may be treated with the herbicidal compounds comprising treatment of the entire plant body while some of plants are treated only on a lower portion of the plant body.

The above-mentioned compound, as an active ingredient, to be used in the controlling method of the present invention can be formulated into a conventional preparation form.

Examples of the preparation form include emulsifiable concentrates, soluble concentrates, emulsions, wettable powders, suspensions and water dispersible granules. See e.g. *Chemistry and Technology of Agrochemical Formulations*, ed. D. A. Knowles, Kluwer Academic Publishers (1998); *Controlled-Release Delivery Systems for Pesticides*, Herbert B. Scher, Marcel Dekker, Inc. (1999).

These preparations can be prepared by a known manner per se. For example, an active ingredient can be mixed with a spreader, i.e., a liquid diluent and/or a solid diluent, using if necessary, a surfactant, i.e., an emulsifier and/or dispersing agent and/or foam forming agent, to prepare a preparation according to the present invention.

When water is used as the spreader, an auxiliary solvent, e.g., an organic solvent, can be used. Examples of the liquid diluent include organic solvents such as aromatic hydrocarbons (e.g., xylene, toluene and alkylnaphthalene), chlorinated aromatic or chlorinated aliphatic hydrocarbons (e.g., chlorobenzenes, ethylene chlorides and methylene chloride), aliphatic hydrocarbons [e.g., cyclohexane or paraffins (e.g., mineral oil fraction, mineral oil and vegetable oil)], alcohols (e.g., butanol and glycol, and ethers or esters thereof), ketones (e.g., acetone, methyl ethyl ketone, methyl isobutyl ketone and cyclohexanone), strong polar solvents (e.g., dimethylformamide and dimethyl sulfoxide), and water.

Examples of the solid diluent include ammonium salts and ground natural minerals (e.g., kaolin, clay, talc, chalk, quartz, attapulgite, montmorillonite and diatomaceous earth), ground synthetic minerals (e.g., highly dispersed silicic acid, alumina and silicate). As the solid carrier for powders, there can be used, ground and classified rocks (e.g., calcite, marble, pumice, sepiolite and dolomite), synthetic particles of inorganic and organic powders, organic substance fine grains (e.g., sawdust, coconut shell, corn cob and tobacco stem) and the like.

The emulsifier includes nonionic and anionic surfactants. Suitable examples of the nonionic surfactant include compounds obtained by addition-polymerizing ethylene oxide to a higher alcohol such as lauryl alcohol, stearyl alcohol and oleyl alcohol; compounds obtained by addition-polymerizing ethylene oxide to an alkyl phenol such as isooctylphenol and nonylphenol; compounds obtained by addition-polymerizing ethylene oxide to an alkyl naphthol such as butylnaphthol and octylnaphthol; compounds obtained by addition-polymerizing ethylene oxide to a higher fatty acid such as palmitic acid, stearic acid and oleic acid; compounds obtained by addition-polymerizing ethylene oxide to an amine such as dodecylamine and stearic acid amine; higher fatty esters of polyhydric alcohols such as sorbitan and compounds obtained by addition-polymerizing ethylene oxide to them; compounds obtained by block-addition-polymerizing ethylene oxide and propylene oxide. Suitable examples of the anionic surfactant include alkyl sulfate salts such as sodium lauryl sulfate and oleyl alcohol sulfate amine salt; alkyl sulfonate salts such as sodium dioctyl sulfosuccinate and sodium 2-ethylhexene sulfonate; aryl sulfonate salts such as sodium isopropylnaphthalene sulfonate, sodium methylenebisnaphthalene sulfonate, sodium ligninsulfonate and sodium dodecylbenzenesulfonate.

As the dispersing agent, for example, lignin sulfite waste liquid or methylcellulose is suitable.

A fixing agent can also be used in the preparation (emulsion), and examples thereof include carboxymethylcellulose, natural or synthetic polymers (e.g., gum Arabic, polyvinyl alcohol and polyvinyl acetate), natural phospholipids (e.g., cephalins and lecithins), and synthetic phospholipids. Further, mineral oils or vegetable oils can also be used as an additive.

A coloring agent can also be used, and the coloring agent includes inorganic pigments (e.g., iron oxide, titanium oxide and Prussian blues), organic dyes such as alizarin dye, azo dye or metal phthalocyanine dye, further, trace elements such as salts of metals, for example, iron, manganese, boron, copper, cobalt, molybdenum and zinc.

The preparation can contain the above-mentioned compounds, as an active ingredient, generally in a concentration of 0.1 to 95 by wt %, preferably 0.5 to 90 by wt %, based on the total weight of the preparation.

In the controlling method of the present invention, the above-mentioned compound, as an active ingredient, can be used in the form of the above-mentioned preparation, and these can be applied, for example, to watering or spraying of the liquid preparation.

The application amount of the compound or the combination of compounds to be used in the method of the present invention can vary appropriately in a substantial range depending on the kind of an active ingredient, growth (exuberant) conditions of morning glory spp., application period, weather conditions and the like. The application amount can be generally in a range of 0.05 to 2.0 kg/ha, preferably 0.1 to 1.5 kg/ha in terms of the amount of the active ingredient.

Depending on the particular application conditions and parameters, such as leave-stages of morning glory, crop and spraying means, the weed control can be effective in a more narrow range of application rate of from 0.05 to 1 kg/ha, preferably 0.1 to 0.8 kg/ha of the amount of the active ingredient, preferably glufosinate (salts).

Preferred is the control of morning glory spp. in soybean using the method of the present invention. The method can be preferably carried out in a soybean field were the soybean plants are set in rows, and the herbicidal compound or compound mixture is applied by spraying devices which direct the spray drizzle to the portion of morning glory below the level of the leaves of the soybean plants and between the rows of the soybean plants, thus avoiding substantial treatment of the soybean plants. Spraying devices which can be used in the method of the invention are commercially available or can be set up on the basis of existing spraying devices by modifying the position and/or direction of the nozzles or jets. Similar preferred treatments as described for soybean crops are also appropriate for other crops, correspondingly.

The invention is further described by the following non-limiting examples which further illustrate the invention, and are not intended, nor should they be interpreted to, limit the scope of the invention.

EXAMPLES

Biological Test Example

Test herbicide in Test Examples 1 and 2
  Glufosinate: In all tests the glufosinate is used as glufosinate solution (commercially available product) containing the active ingredient in an amount of 18.5% in the form of its ammonium salt, also abbreviated as "glufosinate (salt)".

Test Example 1

Morning Glory spp. Control Test

Herbicidal property of glufosinate (salt) on morning glory spp:

In the case of spraying of glufosinate (salt) only on the lower half portion of a hill of morning glory spp:

*Ipomoea hederacea* Jacq. and *Ipomoea triloba* L. generated in the form of grapevine and at the edge of a soybean field in Anjo City, Aichi Prefecture were tested. A 200-fold diluted solution of glufosinate was sprayed only on the lower half portion of the hill while covering the upper half portion thereof with plastic film so that the solution was not sprayed thereon. Thereafter, effects on the lower and upper half portions were observed.

In the case of spraying of glufosinate (salt) only on the upper portion of morning glory spp:

*Ipomoea lacunosa* L. (eight leaves) in a pot was tested. A 200-fold diluted solution of glufosinate (salt) was sprayed only on the upper portion of a stem while preventing spraying on the lower portion thereof. Thereafter, effects on respective portions were observed.

Result and Consideration:

1. Glufosinate (salt) showed a high activity on all of the tested morning glory spp., *Abutilon theophrasti*, *Sida spinosa* L., HIROHAFUURINHOZUKI, *Aeschynomene indica* and *Solanum carolinense*. A high activity was shown particularly on morning glory spp., even at a low herbicidal amount of 100 mL/10 a. Pentazone as a reference herbicide showed a lower activity on morning glory spp. as previously reported, while showed a high activity on *Abutilon theophrasti*. Further, glyphosate isopropylammonium showed specifically slow manifestation of the activity on these plants, and the activity was insufficient particularly on morning glory spp. at the field level in this test range.

2. When glufosinate (salt) was sprayed only on the lower half portion of the hill of morning glory spp., its activity appeared not only in the lower half portion of the hill but also in the peak thereof (see Table 1). This phenomenon appeared first at the peak portion of the hill, thereafter, appeared at the lower portions sequentially. In contrast, when glufosinate was sprayed only on the upper portion of the stem, the effect was observed in one to two leaves under the sprayed region, while the effect was not observed in the lower leaves and in root (see Table 2).

TABLE 1

Effect of glufosinate (salt) spraying on a lower half portion of a hill of morning glory spp. exerted on an upper half portion thereof

| Portion | Glufosinate sprayed portion (•) | Ipomoea hederacea Jacq. | Ipomoea triloba L. |
|---|---|---|---|
| Upper half | | +++ | +++ |
| Lower half | • | +++ | +++ |

Conditions:
Test place: Anjo City, Aichi Prefecture (soybean field)
Treating day: Aug. 13, 2005
Examination date: August 23
Glufosinate (salt) spray: Hills in the form of grapevine having a length of around 70 cm were used as subjects, and a 200-fold diluted solution was sprayed on the lower half portion of the hills
Effect: +++ complete death, ++ almost death, + partial death, − no effect

TABLE 2

Effect of glufosinate (salt) spraying on an upper portion of a stem of *Ipomoea lacunosa L.* exerted on a lower portion thereof

| Portion in terms of the number of leaves | Glufosinate-sprayed region (•) | Effect |
|---|---|---|
| Peak portion of stem | • | +++ |
| 8 | • | +++ |
| 7 | • | +++ |
| 6 | | ++ |
| 5 | | ++ |
| 4 | | − |
| 3 | | − |
| 2 | | − |
| 1 | | − |
| Root | | − |

Conditions:
Test place: Kashiwa City, Chiba Prefecture (pot test)
Treating day: Oct. 23, 2005
Examination date: November 6, cotyledons defoliated at the time of spraying
Glufosinate spray: A 200-fold diluted solution was sprayed on from a peak portion of the stem of morning glory spp. in the form of grapevine to an approximately intermediate site between the sixth and the seventh leaves
Effect: +++ complete death, ++ almost death, + partial death, − no effect Test Example 2

Fact and Superiority of Weedkilling by a Control Machine-Spraying of Glufosinate (Salt) on Soybean Inter-Ridge During its Growth Period Soybean cultivation in the Tokai region is often carried out with large scale by farming associates and large scale farmhouses. Under such circumstances, morning glory spp. cause a serious problem in soybean fields during its growth period, and its controlling method is required to be established quickly. In soybean fields in Anjo City, Aichi Prefecture showing a problem of morning glory spp., a test for proving applicability of controlling morning glory spp. was performed using a control machine-spraying intending laborsaving.

1. Grain Farming Summary and Experimental Method

A grain farming summary and an experimental method are shown in Table 3.

TABLE 3

Grain farming summary and test method

| | |
|---|---|
| Test place: | Izumi, Anjo city, Aichi prefecture |
| Test field scale: | 30 a |
| Dissemination date: | Jun. 27, 2005 |
| Ridge width: | 70 cm |
| Glufosinate (salt) spraying date: | August 9 |
| Soybean height in spraying: | 50 to 55 cm |
| Herbicide amount: | 500 mL/10 a |
| Water amount: | 100 L/10 a |
| Main weeds in spraying: | *Ipomoea triloba L., Ipomoea hederacea Jacq., Ipomoea hederecea Jacq.* var. *integriuscula A.* Gray, *Ipomoea coccinea L., Aeschynomene indica, Digitaria ciliaris* and Japanese barnyard millets (*Echinochloa esculenta* spp.) |
| Spraying nozzle: | soybean inter-ridge herbicide spraying nozzle (manufactured by Maruyama Seisakusho) |
| Setting of non-treated district: | three non-treated districts of 168 m² set in the same field |
| Crop date: | November 11 |
| Crop check: | 4.2 m² (3 ridge × 2 m) whole stem reaping and measuring of weight of bean after air drying |

2. Result and Consideration

1) Spraying Nozzle, Spraying Theory, Actual Spraying

Spraying circumstances are shown in FIGS. 1 and 2. A commercially available spraying apparatus was attached to the front side of a riding-type control machine, and glufosinate was sprayed from near ground edge. The nozzle position can be varied depending on ridge width and soybean height. In a theory of spraying a herbicide, the herbicide is introduced from a herbicide tank through a hose so that the herbicide can be sprayed on a lower part between ridges (suspending mode). Some farmhouses devise by themselves this spraying apparatus. The spraying period in this procedure was 45 minutes/30 a, and the herbicidal time was significantly shortened.

2) Herbicidal Effect and Scattered Phytotoxicity after Spraying

In spraying (FIGS. 1, 2 and 3), morning glory spp. developed almost all over the field, and some of them coiled around soybean, the peak portion thereof extending up to over the head portion of soybean. FIG. 1 is a photograph showing full view of glufosinate spraying. FIG. 2 is a photograph showing glufosinate (salt) sprayed part. FIG. 3 is a photograph showing a herbicidal process of glufosinate (salt). In FIG. 3, an upper stage shows a photograph immediately before spraying (August 9), a middle stage shows a photograph 4 days after spraying (August 13), and a lower stage shows a photograph 14 days after spraying (August 23). FIG. 4 is a photograph showing the killing effect of glufosinate (salt) ranging to the peak portion (shown with an arrow) of the stem of *Ipomoea triloba* L. (14 days after spraying, August 23). As apparent from the above-mentioned photographs, the herbicidal effect of glufosinate (salt) was observed from the next day after spraying, and 4 days after spraying, most of leaves at grapevine-form parts of the morning glory spp. died. This effect appeared even in the peak portion of the stem extending up to over the head portion of the soybean, and in this portion, leaves and stems of morning glory spp. turned to yellow. 14 days after spraying, though some individuals did not die completely, most of the morning glory spp. died up to the peak portion of the stem (FIGS. 3, 4). Phytotoxicity in the case of scattering to soybean was observed in the cotyledon and the first leaf, however, little phytotoxicity was observed in the upper leaves. From these phenomena, it was believed that the morning glory spp. show very higher sensitivity to glufosinate (salt) than soybean.

3) Effect on Bean Weight of Soybean

In non-glufosinate (salt)-sprayed districts, morning glory spp. elongated so as to cover the whole field, and soybean had a lot of abnormal shape hills including falling, folding, twisting and the like. As a result, while the bean weight was 193 kg/10 a in the glufosinate-sprayed district, in the non-glufosinate (salt)-sprayed district, the weight decreased remarkably to as low as 96 kg/10 a, revealing remarkable herbicidal effect (see Table 4).

From the various results described above, spraying of glufosinate (salt) by a control machine in a soybean field during its growing period is a weed controlling technology of high popularization, and dissemination thereof in the further is expected. Further, it was clarified that glufosinate (salt) has an action of killing even up to the peak portion of a stem with generating scarce phytotoxicity in soybean by spraying on only the lower portion of a stem of morning glory spp.

TABLE 4

Effect of weedkilling by spraying glufosinate (salt) with a control machine in a soybean field with rampant morning glory spp. exerted on the bean weight of soybean

| District | Bean weight (kg/10 a) |
| --- | --- |
| Glufosinate (salt)-sprayed district | 193 ± 29 |
| Non-glufosinate (salt)-sprayed district | 96 ± 21 |

Test Example 3

Morning Glory spp. Control Test by Diquat-Paraquat Mixed Solution

Test method: Commercially available morning glories having a height of 70 cm to 100 cm cultivated in a pot were tested. A diquat-paraquat solution (active ingredient amounts, diquat:paraquat=7%:5%, diquat dibromid and paraquat dichloride used, amounts calculated for diquat and paraquat) was sprayed using a hand sprayer on the lower portion of the plant up to 20 cm position (mixed solution amount: 1000 mL/10 a, water: 100 L/10 a). In this operation, the plant was covered with a bag so that the solution did not scatter over the 20 cm position thereby to prevent the scattering of the solution. Thereafter, the herbicidal effect was observed 1 week after and 2 weeks after.

Result: The morning glory died up to the peak portion at 1 week after and 2 weeks after observations.

Figure 6:
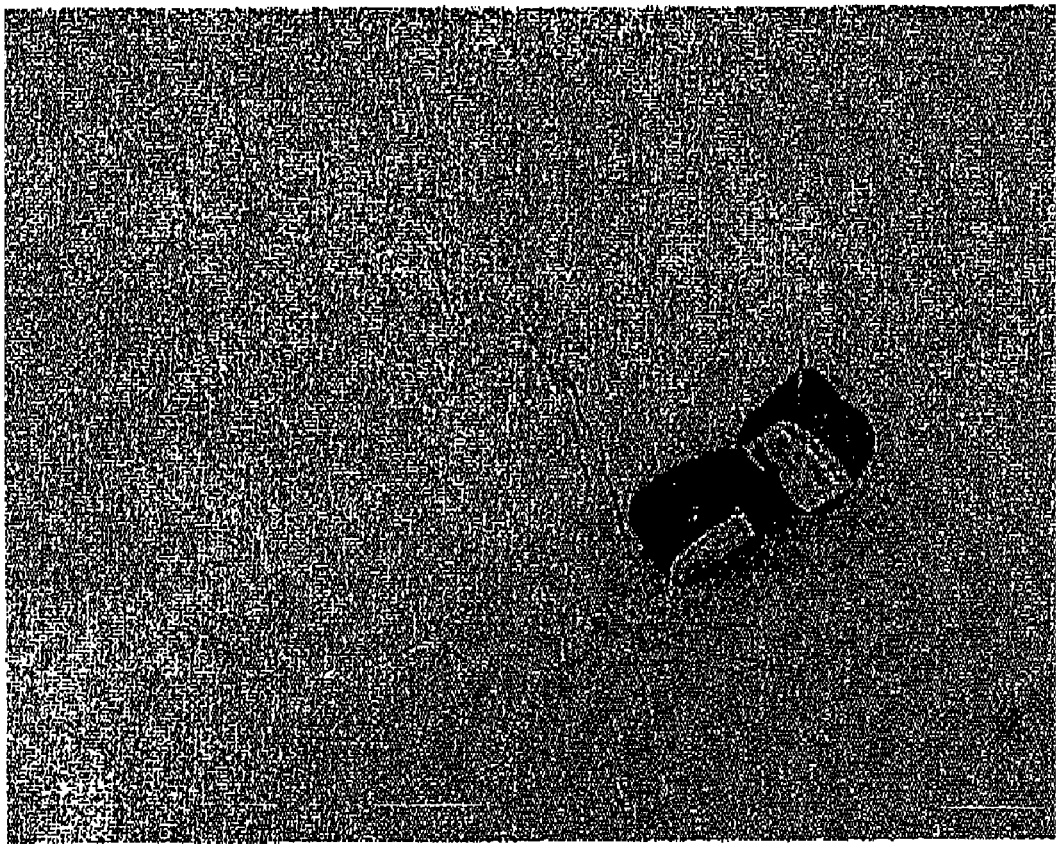
FIG. 6 is a photograph showing a killing effect (2 weeks after spraying) of diquat-paraquat (salts) mixed solution.

Conditions immediately after and 2 weeks after spraying are shown in appended photographs (FIGS. 5 and 6).

Test Example 4

Morning Glory spp. Control Test with Bialaphos Solution

Test Method:
On Aug. 9, 2005, a bialaphos solution (active ingredient amount: 18%, used in the form of the sodium salt bialaphossodium, amount calculated for bialaphos) was sprayed (solution amount: 500 to 1500 mL/10 a, water amount: 100 L/10 a) to morning glory spp. (height: 55 cm to 70 cm) such as *Ipomoea triloba* L. and *Ipomoea hederacea* Jacq. generated between ridges in a soybean field and coiled around soybean, from land surface up to a height of 20 cm above ground, and the herbicidal effect thereafter was observed.

Result: The effect was observed from the next day after the treatment, and 1 week after, the morning glory spp. died up to the peak portion of vine in every test section (solution amount: 500 mL/10 a, 1000 mL/10 a, and 1500 mL/10 a).

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method of selectively controlling morning glory spp. comprising treating a lower portion of a hill rather than the entire hill of morning glory spp. with one or more herbicidal compounds selected from a group consisting of glufosinate, L-glufosinate, bialaphos, paraquat, diquat and agriculturally acceptable salts of the compounds.

2. The method as claimed in claim 1, wherein the herbicidal compound is glufosinate or L-glufosinate or an agriculturally acceptable salt of glufosinate or of L-glufosinate.

3. The method as claimed in claim 1, wherein the selective control is performed in a crop.

4. The method as claimed in claim 3, wherein the crop is a soybean cultivation, fruit cultivation or cotton cultivation.

5. The method as claimed in claim 1, wherein the herbicidal compound or herbicidal compound combination is applied at an application rate of 0.05 to 2.0 kg/ha.

6. The method as claimed in claim 3, wherein the herbicidal compound or herbicidal compound combination is applied by spraying devices which direct the spray drizzle to the portion of morning glory below the level of the leaves of the crop plants and between the crop plants.

7. The method as claimed in claim 6, wherein the crop plant is soybean.

8. The method as claimed in claim 6, wherein the herbicidal compound or the herbicidal compound combination is applied at an application rate of 0.05 to 2.0 kg/ha.

9. The method as claimed in claim 8, wherein the herbicidal compound is glufosinate or L-glufosinate or an agriculturally acceptable salt of glufosinate or of L-glufosinate.

10. The method as claimed in claim 6, wherein the herbicidal compound is selected from the group consisting of paraquat, diquat and agriculturally acceptable salts thereof.

11. The method as claimed in claim 10, wherein the herbicidal compound combination is paraquat dichloride and diquat dibromide.

12. The method as claimed in claim 6, wherein the herbicidal compound is selected from the group consisting of bialaphos and agriculturally acceptable salts thereof.

13. The method as claimed in claim 12, wherein the herbicidal compound is bialaphos sodium.

* * * * *